Figure 1:
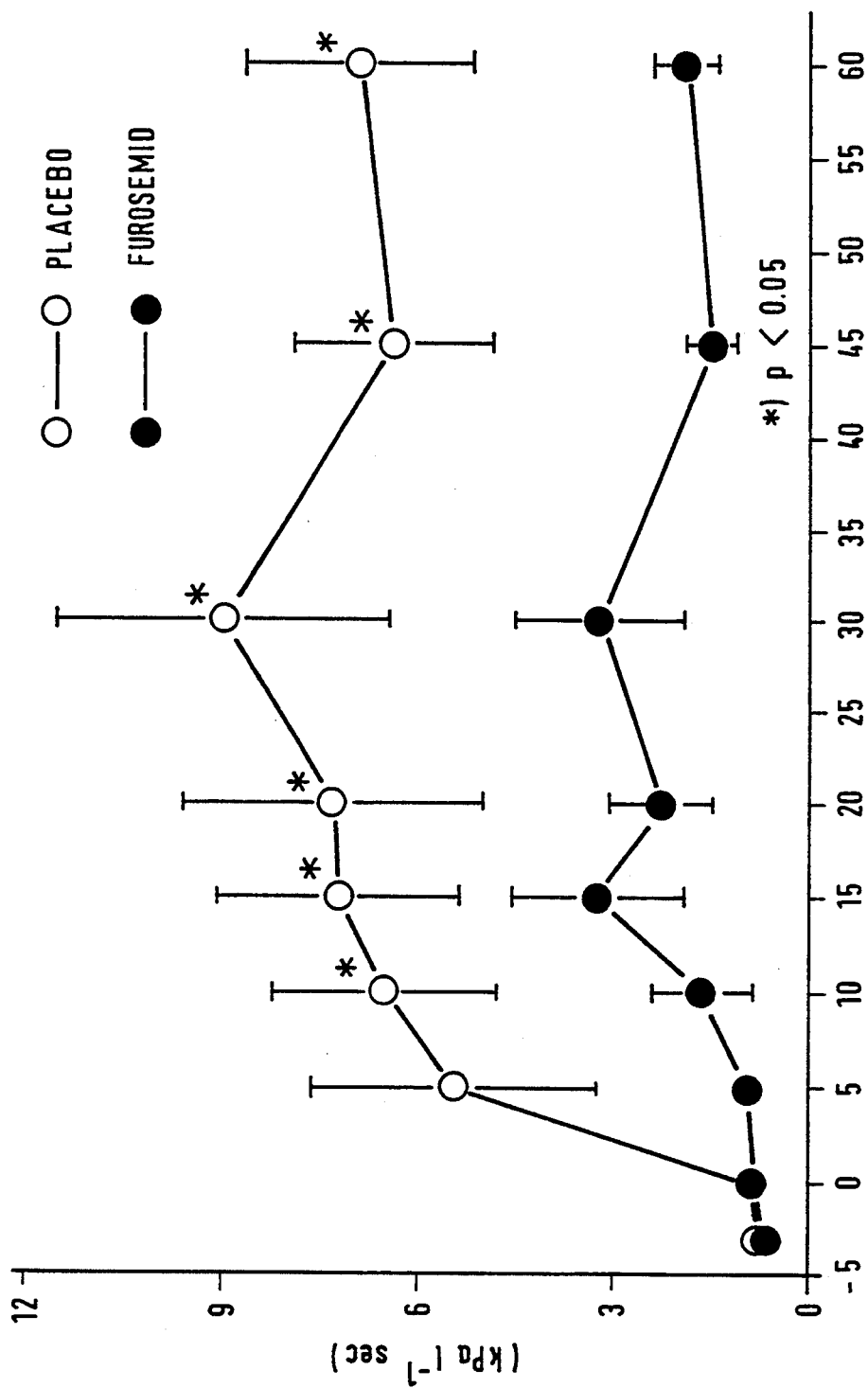
Figure 2A:
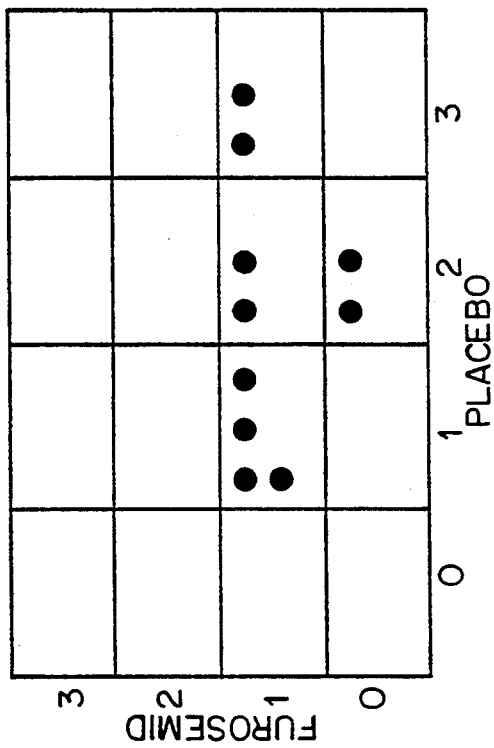
Figure 2B:
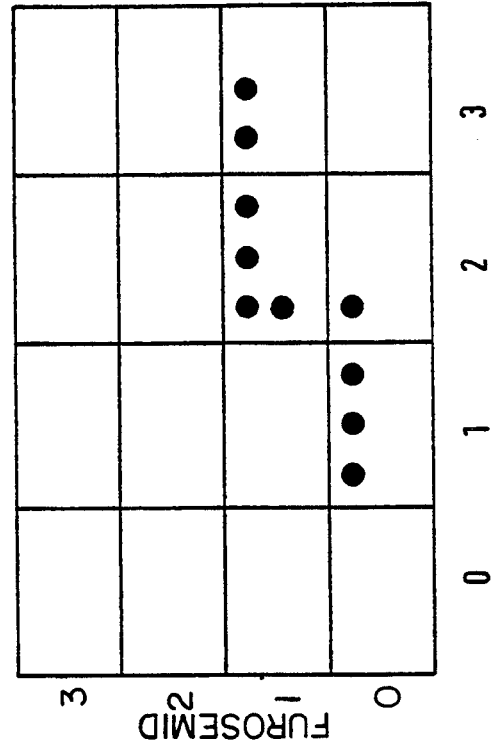
Figure 2C:
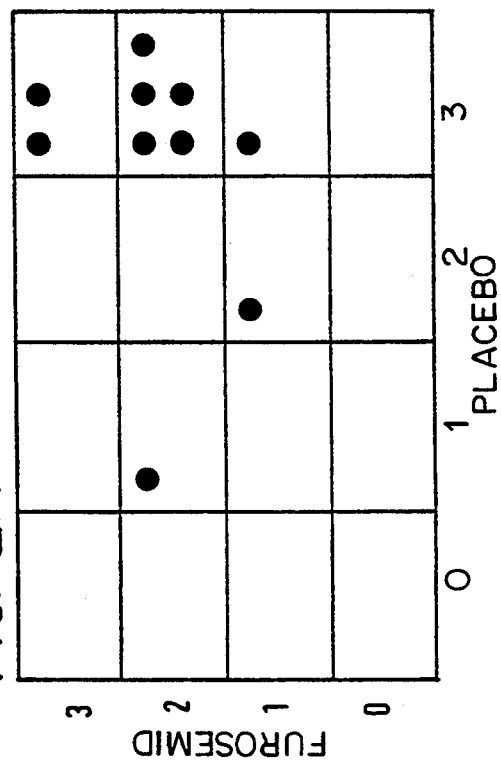
Figure 2D:
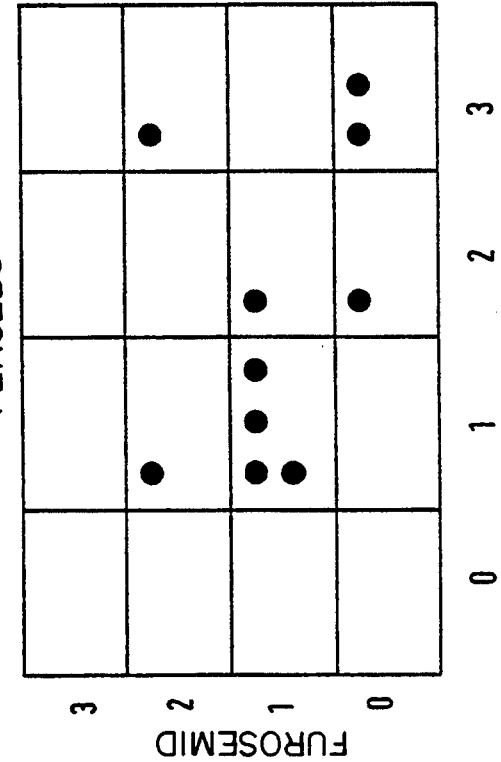

United States Patent [19]

Bianco

[11] Patent Number: 5,392,767

[45] Date of Patent: Feb. 28, 1995

[54] USE OF INHALED LOOP DIURETICS FOR TREATING ALLERGEN-INDUCED NASAL REACTIONS

[75] Inventor: Sebastiano Bianco, Milan, Italy

[73] Assignee: Hoechst Aktiengesellschaft, Frankfurt am Main, Germany

[21] Appl. No.: 789,446

[22] Filed: Nov. 7, 1991

Related U.S. Application Data

[63] Continuation of Ser. No. 487,895, Mar. 6, 1990, abandoned.

[30] Foreign Application Priority Data

Mar. 8, 1989 [DE] Germany ............................ 3907414

[51] Int. Cl.$^6$ ............................................ A61M 11/00
[52] U.S. Cl. ............................ 128/200.14; 128/200.16
[58] Field of Search ............................... 514/314, 471; 128/200.14, 200.16

[56] References Cited

U.S. PATENT DOCUMENTS 4,677,975  7/1987  Edgar et al. .................. 128/200.14
4,886,811  12/1989  Jones et al. ........................ 514/314
4,908,382  3/1990  Bianco ............................... 514/471

FOREIGN PATENT DOCUMENTS 3500M  8/1965  France .

OTHER PUBLICATIONS

S. Bianco, et al., "Prevention of Exercise-Induced Bronchoconstriction by Inhaled Frusemide," The Lancet, pp. 252–255 (1988).

American Lung Association, American Thoracic Society, 1988 Annual Meeting Supplement, Abstracts, vol. 137(4), (1988).

Primary Examiner—Edgar S. Burr
Assistant Examiner—Aaron J. Lewis
Attorney, Agent, or Firm—Finnegan, Henderson, Farabow, Garrett & Dunner

[57] ABSTRACT

Loop diuretics, particularly their well known representative furosemide, are effective drugs for the treatment of allergen-induced nasal reactions, if a solution of the loop diuretic is nebulized into the nostrils.

3 Claims, 5 Drawing Sheets

USE OF INHALED LOOP DIURETICS FOR TREATING ALLERGEN-INDUCED NASAL REACTIONS

This application is a continuation of application Ser. No. 07/487,895, filed Mar. 6, 1990, now abandoned.

This invention relates to the use of loop diuretics for treating allergen-induced nasal reactions and to a method which comprises nebulizing a solution of loop diuretic into the nostrils for treating allergen induced nasal reactions.

Loop diuretics are a well known diuretic agents, a well known representative is furosemide of the formula I

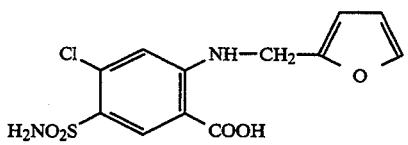

and its effects have been studied extensively. The drug is usually given orally but can be used intravenously to promote diuresis.

Furosemide also turned out to be an agent for preventing or treating asthma (see The Lancet, Jul. 30, 1988, p. 252).

But there was no suggestion in any one of these citations to use loop diuretics in combating allergic reactions of the nasal mucosa. Loop diuretics are for instance bumetanid, ethacrynic acid, etolozine or piretanide, torasemide, indacrinon, azosemide, besides furosemide.

To investigate whether furosemide, one of the typical representatives of the loop diuretics has a protective activity on the allergic reactions in the nasal mucosa a double-blind, placebo-controlled, randomized crossover study on the effect of inhaled furosemide on the response to nasal allergen challenge was performed.

PATIENTS AND METHODS

PATIENTS: Ten volunteers with allergic rhinitis, 4 male and 6 female, age range 14 to 35 years (mean $21.9 \pm 1.9$), were recruited among patients showing a positive response to specific nasal challenge. They all had a clinical history of allergic thiniris, a positive immediate skin reaction to the relevant allergen, were asymptomatic or with very mild respiratory symptoms, had been free of respiratory infections for at least 4 weeks and where not taking therapy. Four of the patients were allergic to pollen and 6 to Dermatophagoides. Patients allergic to pollens were investigated outside the pollen season. In a preliminary challenge, 2 puffs allergen (Alpha Base, Dome/Hollister-Stier, Bayropharm Italia, Milan, Italy), were administered locally in a single nostril by means of a nasal nebulizer delivering 80 $\mu$l/puff. Nasal resistance for each nostril was measured before challenge and after 5, 10, 15, 20, 30, 45 and 60 minutes by anterior rhinomerry (Mod. NR4, Mercury electronics Scotland Ltd, Glasgow, UK). Nasal resistance was measured separately for each nostril by recording the air flow when the pressure at the controlateral side reached the sample point of 150 Pa. Resistance was then calculated as the ratio between controlateral pressure (i.e. 150 Pa) and flow (see: Clement PAR. Committee report on standardization of rhinomanometry. Rhinology 1984; 22:151-5). Total nasal resistance was calculated when required with the formula $(R_1 \times R_2)/(R_1 + R_2)$, where $R_1$ and $R_2$ are the values obtained for each single nostril. Patients showing at least a 100% increase from baseline of the resistance at the stimulated nostril at any time point were considered as positive.

STUDY DESIGN

The effect of pre-treatment with inhaled furosemide on nasal allergic response was investigated in a randomized, double blind, cross-over study against placebo. Each patient performed two specific nasal challenges within an interval of 4 to 8 days, using the same protocol and the same allergen dose as in the preliminary challenge. Immediately before the administration of the allergen, the patients received in both nostrils 2 puffs of either furosemide 10 mg/ml in NaCl 7.0 mg+NaOH q.s. ad pH 9+$H_2O$ q.s. ad 1 ml, 295 mOsm/kg, pH 8.36 (®Lasix, Hoechst AG, Frankfurt am Main, West Germany) or the diluent alone without furosemide (placebo), given by means of a nasal nebulizer delivering 120 $\mu$l/puff. Nasal resistance was measured before and after pretreatment, and at 5, 10, 15, 20, 30, 45 and 60 minutes after challenge. To obtain an unbiased estimate of challenge-induced rhinorrhea, nasal secretions were collected for 30 minutes after challenge using gauze carefully inserted in the nostrils, and the amount of secretion was calculated as the final weight of the gauze minus the original dry weight. Nasal symptoms (pruritus, nasal obstruction, sneeze, lachrymation) were evaluated by an arbitrary subjective score ranging from 0 (absent) to 3 (maximum).

DATA ANALYSIS

Data were expressed as absolute values or as the difference from baseline values at time zero, i.e. after treatment with furosemide or placebo and immediately before allergen challenge.

The percentage protective effect was calculated for each patient according to the formula: (AUC furosemide—AUC placebo)/AUC placebo$\times$100, where AUC is the area under the time-response curve, expressed in absolute differences from baseline.

The two-way analysis of variance and the paired Student's t test were used for statistical comparison of normally distributed variables (Snidercor WG, Cochran WG. Statistical methods, 7th ed. Ames, Iowa University Press, 1980). The McNemar test was used for comparison of symptom scores. A level of p of 0.05 was considered as significant.

RESULTS

Total nasal resistance measured by anterior rhinomanometry before challenge was $0.39 \pm 0.07$ kPa$\cdot 1^{-1}$.sec (M$\pm$SE) before placebo and $0.38 \pm 0.06$ before furosemide. Local treatment with furosemide or placebo did not change significantly these parameters.

After placebo, all the patients developed an immediate obstructive nasal reaction in the stimulated nostril, beginning between 30 seconds and 20 minutes from challenge, reaching a maximum at 10 to 30 minutes, and lasting more than 60 minutes. Nasal resistance was increased compared to post-placebo baseline at each time point after challenge, and maximum variation was $13.7 \pm 2.5$. By contrast, no significant changes of nasal resistance were observed in the unstimulated nostril (maximum variation 3.9±2.4, table I and FIG. 1) although in two cases a marked increase of resistance was observed also at this side. All the patients developed some degree of sneeze, lachrymation, nasal pruritus (FIGS. 2A-2D), and rhinorrhea (4.15±0.77 g, rig. 3).

Figure 3:
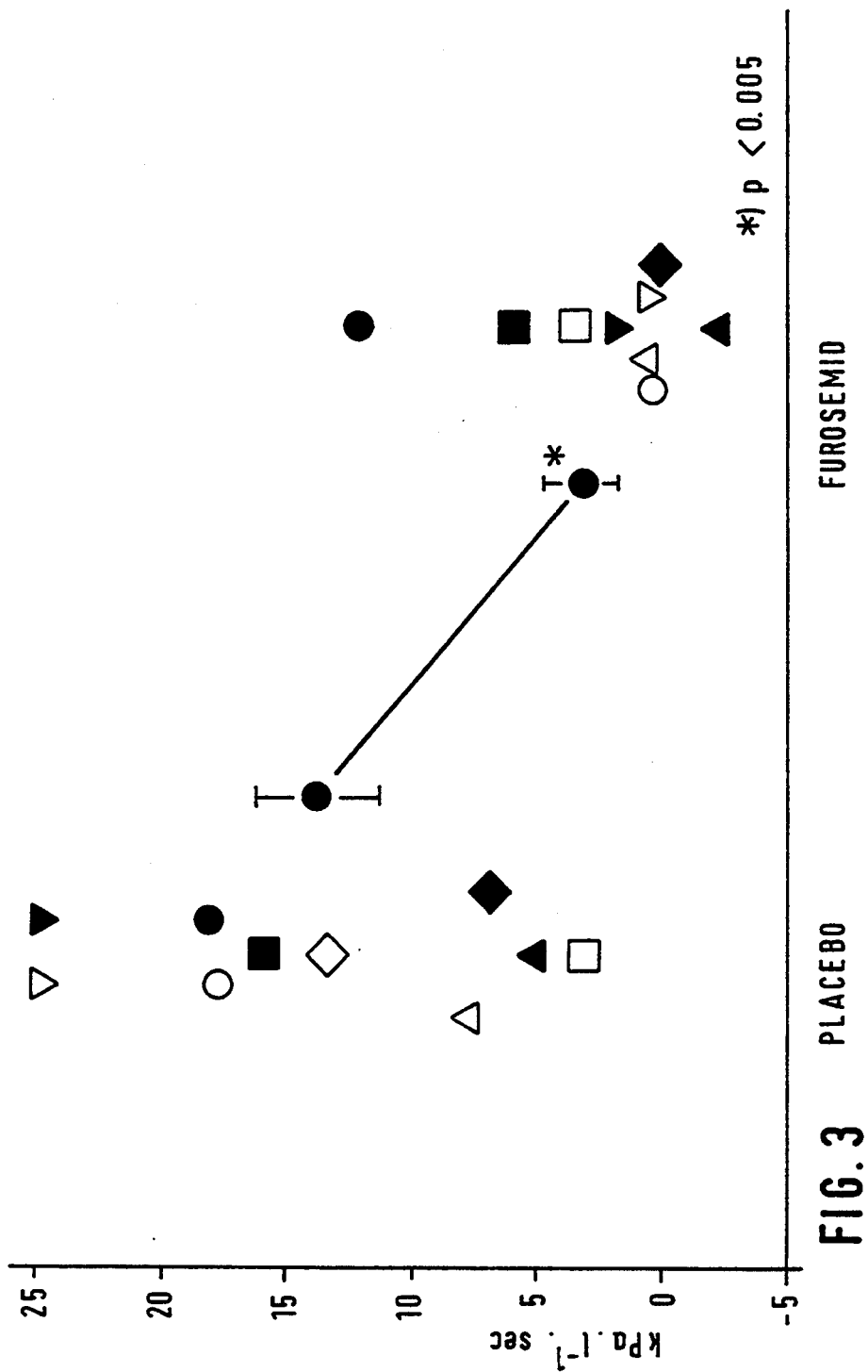
Figure 4:
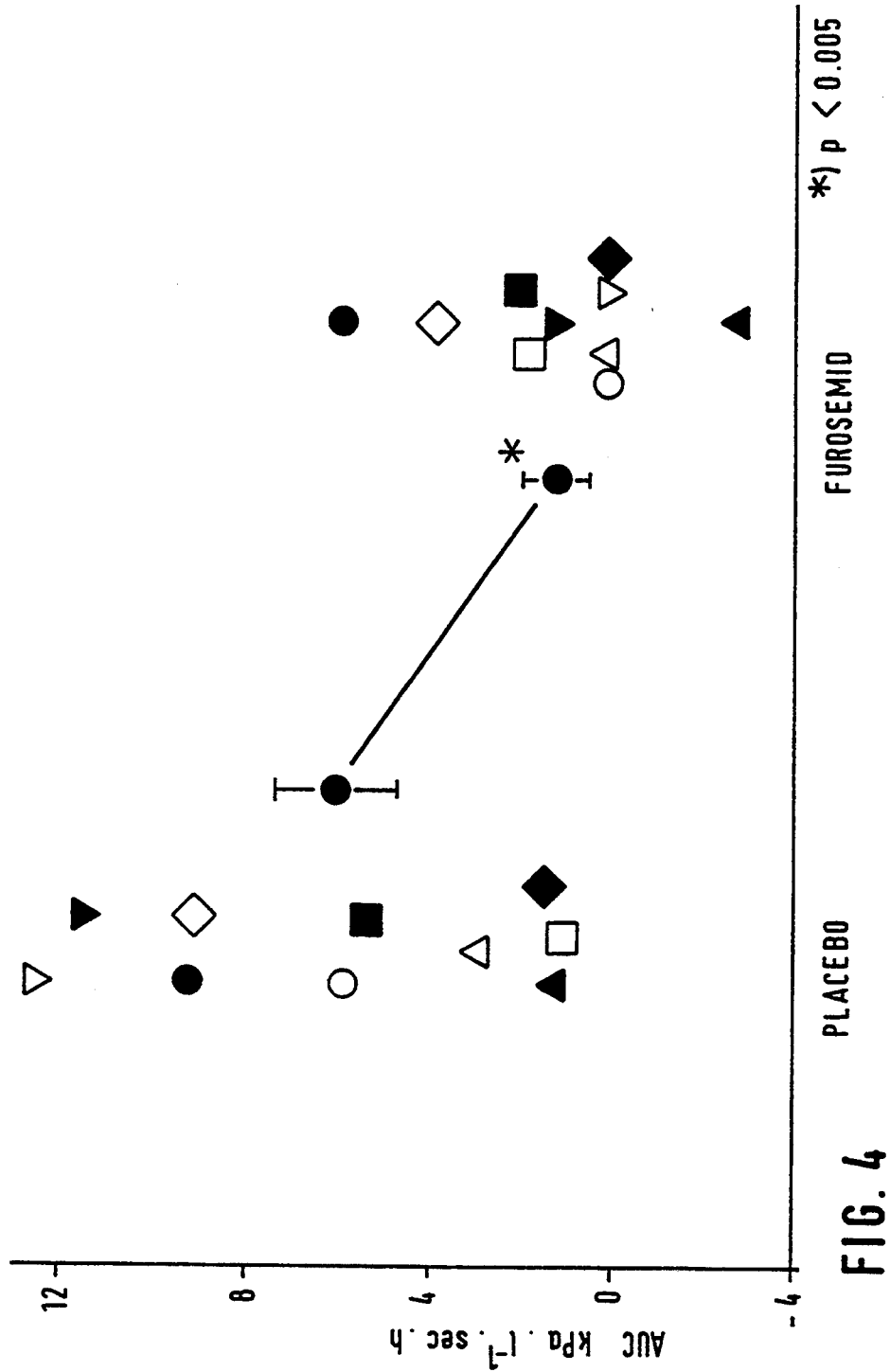

After furosemide, allergen-induced increase of nasal resistance was markedly reduced compared to placebo for all the course of the experiment (FIG. 1), and maximum variation of resistance in the stimulated nostril was 3.1±1.4 (p<0.005 vs. test after placebo, FIG. 4). Protective activity of furosemide compared to placebo, evaluated by AUC, was 87±30% (FIG. 5), most of the variability being due to a single patient who showed a poor response after placebo which was not protected by furosemide. No significant variations were observed in the unstimulated nostril (maximum variation 0.6±0.5), even in the two subjects who had shown a controlateral reaction after placebo. Symptom scores were also reduced in most cases, particularly nasal pruritus (p>0.05) and lachrymation (p<0.005, FIGS. 2A-2D), and nasal secretion was greatly reduced compared to placebo (1.63±0.5 g, p<0.001, FIG. 3).

DISCUSSION

Local treatment with furosemide markedly reduced nasal obstruction, secretion and symptoms induced by specific allergen challenge. This effect was specific, as no changes were observed after furosemide or placebo alone, and was observed in virtually all patients.

FIGURE LEGENDS

FIG. 1—Changes of nasal airway resistance in the stimulated nostril after pretreatment with furosemide (open circles) or placebo (solid circles). *) p<0.005 vs. baseline.

FIGS. 2A-2D—Changes of symptom scores elicited by nasal challenge after treatment with furosemide or placebo.

FIG. 3—Total nasal discharge collected in the 60 minutes following allergen challenge after placebo (left) or furosemide (right). *) p<0.001 rs. placebo. Each symbol represents a single patient. Circles with error bars represent mean and standard error of the whole group after each treatment.

FIG. 4—Maximum increase from baseline of nasal resistance at the stimulated nostril after pretreatment with placebo or furosemide. *) p<0.005. Other symbols as in FIG. 3.

Figure 5:
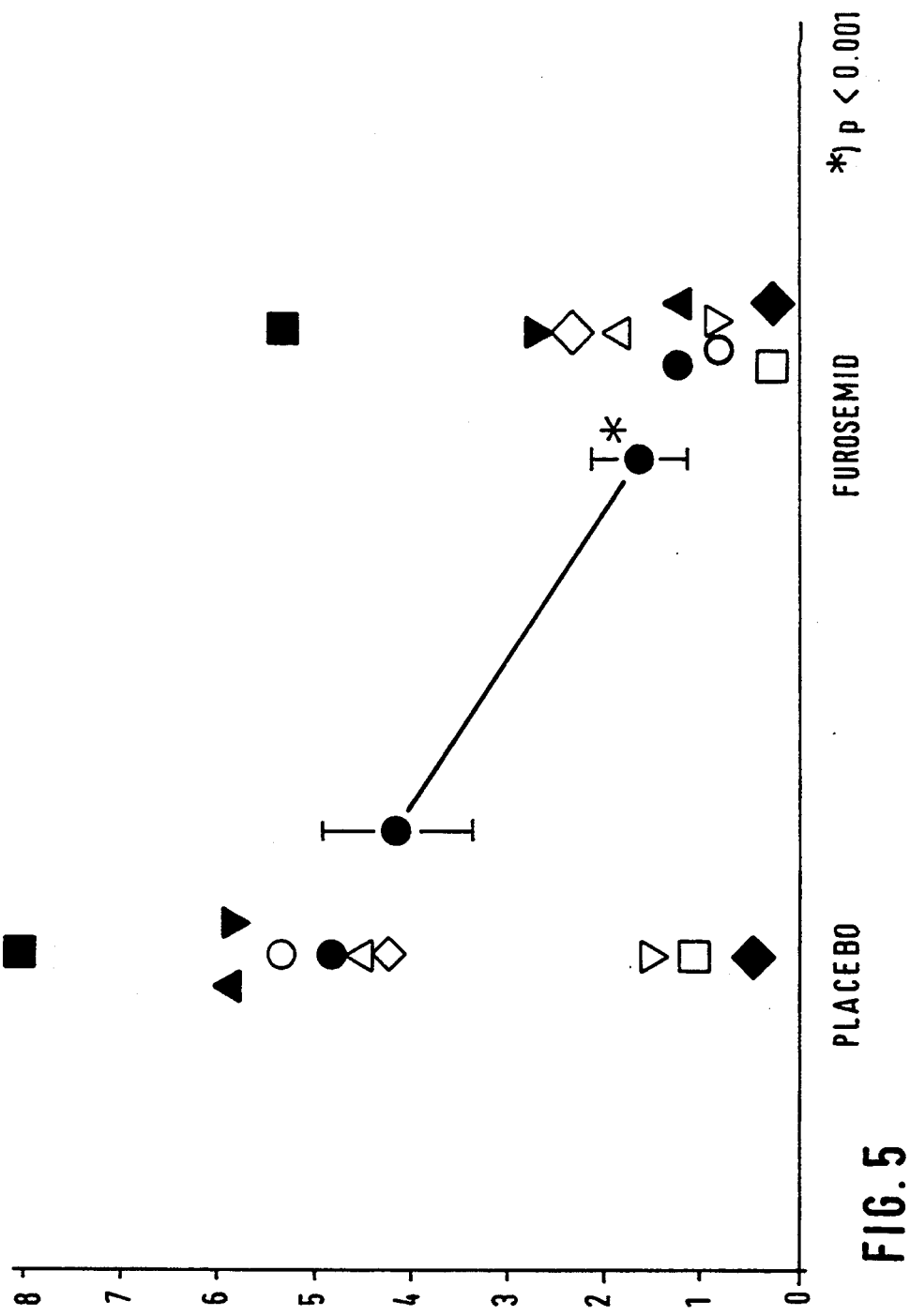

FIG. 5—Area under the time-course curve of nasal resistance changes during 60 minutes after challenge preceeded by treatment with placebo or furosemide. Symbols as in FIG. 3.

TABLE I

Effect of furosemide or placebo on changes of nasal airways resistance after allergen challenge.

| time (minutes) | STIMULATED SIDE | | UNSTIMULATED SIDE | |
|---|---|---|---|---|
| | placebo | furosemide | placebo | furosemide |
| pre-treat.[a] | 0.78 ± 0.13[b] | 0.67 ± 0.18 | 0.87 ± 0.21 | 0.96 ± 0.20 |
| 0 | 0.88 ± 0.19 | 0.83 ± 0.30 | 1.15 ± 0.55 | 1.34 ± 0.32 |
| 5 | 5.44 ± 2.20 | 0.94 ± 0.20 | 1.46 ± 0.66 | 1.13 ± 0.29 |
| 10 | 6.51 ± 7.72[cd] | 1.63 ± 0.76 | 4.57 ± 2.98 | 0.93 ± 0.16 |
| 15 | 7.20 ± 1.86[c] | 3.23 ± 1.34 | 3.56 ± 2.94 | 1.07 ± 0.26 |
| 20 | 7.29 ± 2.30[c] | 2.23 ± 0.78 | 2.47 ± 1.81 | 1.04 ± 0.24 |
| 30 | 8.95 ± 2.56[cd] | 3.18 ± 1.31 | 2.33 ± 1.60 | 1.41 ± 0.42 |
| 45 | 6.35 ± 1.54[cd] | 1.46 ± 0.37 | 1.13 ± 0.27 | 1.24 ± 0.41 |
| 60 | 6.87 ± 1.75[cd] | 1.85 ± 0.48 | 1.38 ± 0.43 | 1.27 ± 0.52 |

[a] Basal measurement before placebo or furosemide treatment
[b] M ± SE
[c] p < 0.05 vs. time 0
[d] p < 0.05 vs. placebo at the same time point

I claim:

1. Method for treating allergen-induced nasal reactions which comprises nebulizing a solution of furosemide into the nostrils.

2. A method for the treatment of allergen-induced nasal reactions which comprises administering into the nose an amount of a loop diuretic effective for treating allergen-induced nasal reactions.

3. The method according to claim 2 which comprises nebulizing into the nose an amount of solution of a loop diuretic effective for treating allergen-induced nasal reactions.

* * * * *